US012613569B2

(12) United States Patent
Jeon

(10) Patent No.: US 12,613,569 B2
(45) Date of Patent: Apr. 28, 2026

(54) SYSTEM AND METHOD FOR PROVIDING VIRTUAL REALITY CONTENTS FOR RELAXATION TRAINING TO STABILIZE PSYCHOLOGICAL STATE OF USER

(71) Applicant: MEDITRIX CO., LTD., Seoul (KR)

(72) Inventor: Hong Jin Jeon, Seoul (KR)

(73) Assignee: SAMSUNG LIFE PUBLIC WELFARE FOUNDATION (KR)

( * ) Notice: Subject to any disclaimer, the term of this patent is extended or adjusted under 35 U.S.C. 154(b) by 1049 days.

(21) Appl. No.: 17/608,358

(22) PCT Filed: Jul. 9, 2021

(86) PCT No.: PCT/KR2021/008801
§ 371 (c)(1),
(2) Date: Nov. 2, 2021

(87) PCT Pub. No.: WO2022/019545
PCT Pub. Date: Jan. 27, 2022

(65) Prior Publication Data
US 2022/0179480 A1     Jun. 9, 2022

(30) Foreign Application Priority Data

Jul. 22, 2020    (KR) ........................ 10-2020-0091292

(51) Int. Cl.
*G06F 3/01* (2006.01)
*A61M 21/00* (2006.01)
(Continued)

(52) U.S. Cl.
CPC ............. *G06F 3/011* (2013.01); *A61M 21/02* (2013.01); *G06F 3/16* (2013.01);
(Continued)

(58) Field of Classification Search
CPC ...... G06F 3/011; G06F 3/16; G06F 2203/011; G06F 3/167; A61M 21/02;
(Continued)

(56) References Cited

U.S. PATENT DOCUMENTS 9,213,403 B1 * 12/2015 Raffle ................... G06F 3/0346
9,380,978 B2 *  7/2016 Reiner ................... G06Q 10/06
(Continued)

FOREIGN PATENT DOCUMENTS

CN          105708436 A  *  6/2016
CN          105893780 B  *  4/2019  .............. A61B 5/02
(Continued)

OTHER PUBLICATIONS

Wilhelm von Rosenberg et al., Resolving Ambiguities in the LF/HF Ratio: LF-HF Scatter Plots for the Categorization of Mental and Physical Stress from HRV, Frontiers in Physiology, Jun. 2017, vol. 8, Art. 360, pp. 1-12.
(Continued)

*Primary Examiner* — Alex M Valvis
*Assistant Examiner* — Julie Thi Tran
(74) *Attorney, Agent, or Firm* — Dilworth IP, LLC

(57) ABSTRACT

A system and method for providing VR (Virtual Reality) content for relation training to stabilize the psychological state of a user which models VR content suitable for the psychological state of the user, based on information of the user, providing the modeled VR contents to the user, analyzes the psychological state of the user based on the provided VR contents, changes the VR contents by reducing the output speed of the VR contents or reducing the change rate of an object, and provides the user with the VR contents remodeled through the change, thereby providing VR contents more suitable for the user.

3 Claims, 6 Drawing Sheets

100

(51) Int. Cl.
    *A61M 21/02*      (2006.01)
    *G06F 3/16*       (2006.01)

(52) U.S. Cl.
    CPC ............... *A61M 2021/0027* (2013.01); *A61M 2021/005* (2013.01); *A61M 2205/507* (2013.01); *G06F 2203/011* (2013.01)

(58) Field of Classification Search
    CPC .... A61M 2021/0027; A61M 2021/005; A61M 2205/507; A61M 2205/50; A61M 2230/04; A61M 2230/06; A61M 2230/42; G16H 40/63; G16H 50/20; G16H 20/70; A61B 5/024; A61B 5/16; A61B 5/02405; A61B 5/165; G06T 19/00; G06T 19/003
    See application file for complete search history.

(56) References Cited

U.S. PATENT DOCUMENTS

| | | | | |
|---|---|---|---|---|
| 9,953,650 | B1 * | 4/2018 | Falevsky ................. | G06F 3/013 |
| 2008/0214903 | A1 * | 9/2008 | Orbach ................... | A61B 5/33 |
| | | | | 705/2 |
| 2014/0316192 | A1 * | 10/2014 | de Zambotti ......... | A61B 5/486 |
| | | | | 600/27 |
| 2014/0378810 | A1 * | 12/2014 | Davis .................... | G06F 16/248 |
| | | | | 600/407 |
| 2017/0119994 | A1 * | 5/2017 | Argaman ............. | A61B 5/0205 |
| 2017/0162072 | A1 * | 6/2017 | Horseman ........... | A61B 5/6803 |
| 2017/0169379 | A1 * | 6/2017 | Horseman ............. | G06Q 10/00 |
| 2018/0089901 | A1 * | 3/2018 | Rober ................... | G06V 20/56 |
| 2018/0190376 | A1 * | 7/2018 | Hill ........................ | A61B 5/375 |
| 2018/0348863 | A1 * | 12/2018 | Aimone ................. | G06F 3/147 |
| 2019/0065970 | A1 * | 2/2019 | Bonutti ................. | G16H 20/10 |
| 2019/0160286 | A1 * | 5/2019 | Yang ................. | A61N 1/36025 |

FOREIGN PATENT DOCUMENTS

| | | | | |
|---|---|---|---|---|
| KR | 10-2019-0020418 | A | 3/2019 | |
| KR | 10-2020-0049930 | A | 2/2022 | |
| WO | WO-2015044851 | A2 * | 4/2015 | ............. A61B 3/113 |

OTHER PUBLICATIONS

European Search Report in EP Patent Application No. 21845807.3 dated Jul. 30, 2024.
Office Action from related KR Application No. 10-2020-0091292 dated Jan. 11, 2022, 7 pages.

* cited by examiner

100

<u>100</u>

<u>130</u>

(a)
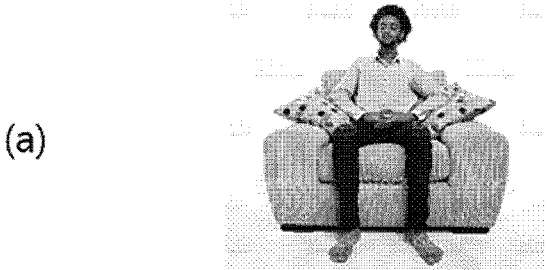
(b)
 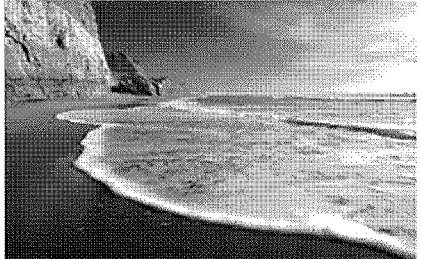
FIG. 4

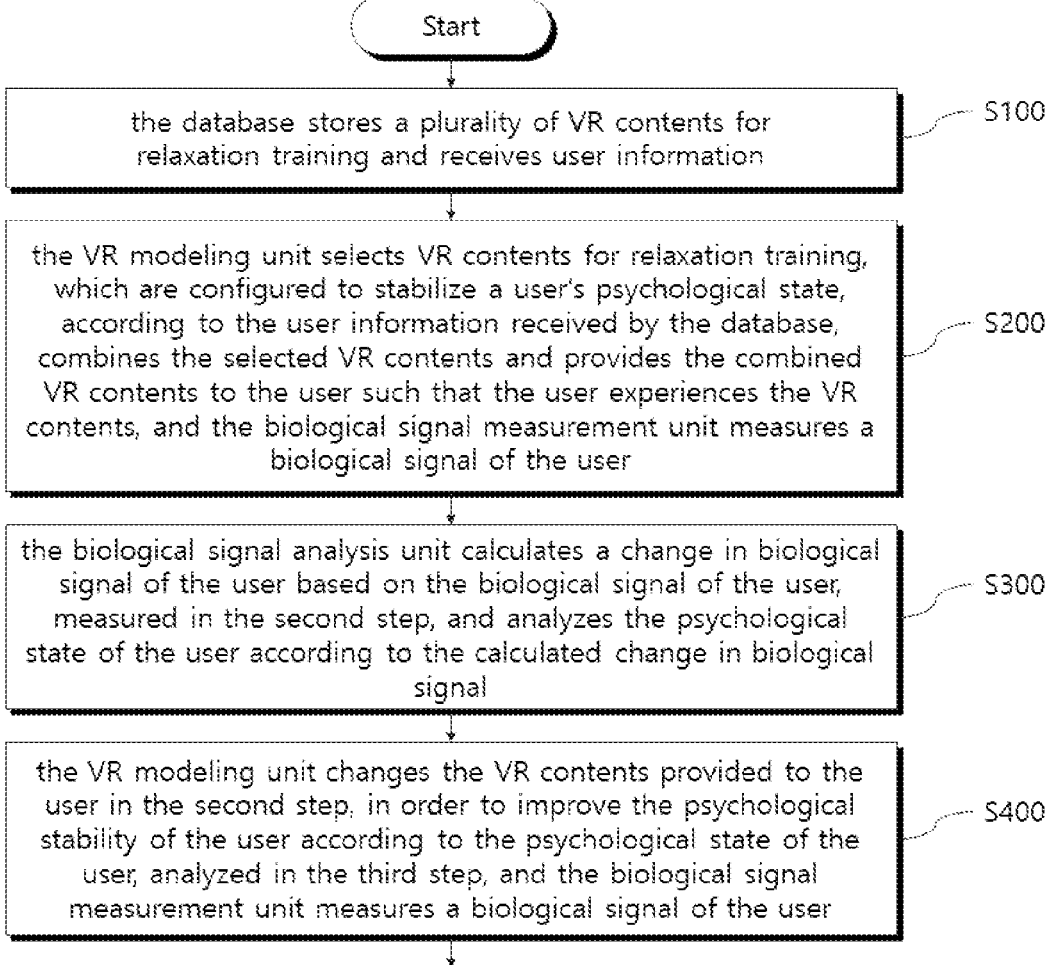

Start the database stores a plurality of VR contents for relaxation training and receives user information — S100 the VR modeling unit selects VR contents for relaxation training, which are configured to stabilize a user's psychological state, according to the user information received by the database, combines the selected VR contents and provides the combined VR contents to the user such that the user experiences the VR contents, and the biological signal measurement unit measures a biological signal of the user — S200 the biological signal analysis unit calculates a change in biological signal of the user based on the biological signal of the user, measured in the second step, and analyzes the psychological state of the user according to the calculated change in biological signal — S300 the VR modeling unit changes the VR contents provided to the user in the second step, in order to improve the psychological stability of the user according to the psychological state of the user, analyzed in the third step, and the biological signal measurement unit measures a biological signal of the user — S400

End

FIG. 5

SYSTEM AND METHOD FOR PROVIDING VIRTUAL REALITY CONTENTS FOR RELAXATION TRAINING TO STABILIZE PSYCHOLOGICAL STATE OF USER

TECHNICAL FIELD

The present disclosure relates to a system for providing VR (Virtual Reality) contents for stabilizing the psychological state of a user through relaxation training and a method for providing virtual reality contents using the same, and particularly, to a system and method for providing VR contents, which model VR contents for relaxation training according to the psychological state of a user, provide the modeled VR contents such that the user experiences the VR contents, and provide VR contents more suitable for the user by analyzing a change in psychological state of the user according to the provided VR contents.

BACKGROUND OF THE INVENTION

Depression is a common mental disease that may cause various problems such as a poor personal relationship or job disruption. In a severe case, depression may cause a serious result such as a suicide. In particular, depression is considered as a kind of cold to modern people.

In most cases, various mental diseases such as depression are caused by complex factors in which a biological factor and a psychological or social factor are combined. In order to treat such mental diseases which are caused by the complex factors, various methods such as exercise, meditation therapy, medicine treatment and psychology counseling are suggested.

However, it is not easy for a patient to try on his/her own to overcome a psychological disorder through the exercise or meditation therapy. Furthermore, although the patient relies on the medicine treatment, it is difficult to expect satisfactory treatment efficiency. The psychological counseling is considered as the most effective method. In many cases, however, patients tend to avoid the psychological counseling due to surrounding peoples' stares.

In consideration of such aspects, a VR (Virtual Reality)-based treatment is currently used to treat a patient who suffers from a phobia such as acrophobia or claustrophobia, among mental diseases. That is, the VR-based treatment exposes a patient to a situation or object that creates a sense of fear, such that the patient is trained to try to avoid the situation on his/her own.

However, when VR is used for mental disease treatment, the exposure training may rather maximize a user's sense of fear, thereby worsening the mental disease.

In order to solve such a problem, one of VR control technologies used for mental disease treatment is disclosed in Korean Patent Application Publication No. 10-2018-0094892 (Patent Document 1) entitled 'Stress Relaxation System and Stress Relaxation Method by the System'. The system and method in accordance with Patent Document 1 may provide VR contents which are provided with breathing training contents which guide and train a user to breathe in a correct breathing pattern in order to relax the user's stress, and drive a motion chair in synchronization with the VR contents, in order to effectively stabilize the psychological state of the user.

However, such a system and method cannot reconstruct the VR contents according to the degree of the user's uneasiness, and thus have difficulties in determining the treatment progress, and taking a proper action or discovering side effects, the proper action including correcting the future treatment plan or changing the treatment method.

SUMMARY OF THE INVENTION

Technical Problem

Various embodiments are directed to a system and method for providing VR contents, which can measure a change in biological signal of a user in real time, analyze the psychological state of the user, and effectively improve the psychological state of the user.

Also, various embodiments are directed to a system and method for providing VR contents, which can provide a plurality of VR contents for relaxation training to a user who suffers from depression and anxiety, analyze the correlation between the provided VR contents and the psychological state of the user, extract only VR contents which have been evaluated to most significantly improve the psychological stability of the user, reconfigure new VR contents, and provide contents suitable for the user.

Technical Solution

The present disclosure relates to a system for providing VR contents for relaxation training to stabilize the psychological stability of a user.

In an embodiment, there is provided a system for providing VR (Virtual Reality) contents for relaxation training to stabilize the psychological state of a user. The system may include: a contents providing unit configured to provide VR contents to a user such that the user experiences the VR contents; a VR modeling unit configured to receive information from the user, model the VR contents for stabilizing the psychological state of the user, based on the received user information, and provide the modeled VR contents to the contents providing unit; a biological signal measurement unit configured to measure a biological signal of the user; and a biological signal analysis unit configured to analyze the psychological state of the user according to the experience of the VR contents, based on a change in the measured biological signal of the user. The VR modeling unit may remodel the VR contents according to the psychological state of the user, analyzed by the biological signal analysis unit.

The VR modeling unit may have a plurality of VR contents each composed of a series of images and sounds, extract VR contents suitable for the psychological state of the user, among the plurality of VR contents, based on the user information received from the user, and provide the extracted VR contents to the contents providing unit.

The VR contents may be configured as a video in which an object changes. The VR modeling unit may change the change speed of the object in the video based on the psychological state of the user, analyzed by the biological signal analysis unit, and provide the changed VR contents to the contents providing unit.

The VR modeling unit may analyze the correlation between the VR contents experienced by the user and the psychological stability of the user, analyzed by the biological signal analysis unit, extract the VR contents that have been evaluated to most significantly improve the psychological stability of the user, among the plurality of VR contents, and store the extracted VR contents in a database with the received user information.

Therefore, the system for providing VR contents in accordance with an aspect of the present disclosure may measure a change in biological signal of a user in real time, analyze the psychological state of the user according to the biological signal, and provide VR contents to effectively improve the psychological stability of the user based on the analysis result.

The biological signal measurement unit may include: a first sensor module configured to measure a biological signal of the user; and a second sensor module configured to measure an HRV (Heart Rate Variability) signal of the user.

The biological signal analysis unit may determine that the psychological stability of the user is low, when the rate of change in the biological signal of the user, measured by the first sensor module, is 20% higher.

Therefore, the system for providing VR contents for relaxation training in accordance with an aspect of the present disclosure may acquire a more accurate measurement value for the psychological stability of the user than when only the heart rate or breathing signal of the user is measured.

In an embodiment, there is provided a method for providing VR contents for relaxation training to a user by using a VR apparatus to stabilize the psychological state of the user. The method may include: providing a plurality of VR contents; an information input step of receiving user information; a first contents providing step of selecting VR contents to stabilize the psychological state of a user according to the received user information, and measuring a biological signal of the user while providing the selected VR contents to the user such that the user experiences the VR contents; an analysis step of calculating a change in the biological signal of the user based on the biological signal of the user, measured in the first contents providing step, and analyzing the psychological state of the user according to the calculated change in the biological signal; and a second contents providing step of changing the VR contents provided in the first contents providing step so as to improve the psychological stability of the user according to the analysis result of the analysis step, and measuring a biological signal of the user.

The method may further include a storage step of analyzing the correlations between the changes in the biological signal of the user, calculated in the first and second VR contents providing steps, and the VR contents provided to the user, extracting the VR contents that have been evaluated to most significantly improve the psychological stability of the user, and storing the extracted VR contents in a database with the received user information.

The analysis step may include determining that the psychological stability of the user is low, when the rate of change in the biological signal of the user is 20% higher, and the VR contents selected in the second contents providing step may be different from the VR contents which are provided in the first contents providing step and in which the psychological stability of the user are determined to be low.

The biological signal of the user may include an HRV signal, and the VR contents where the psychological stability of the user may be the highest are VR contents where the LF/HF ratio mean value of the HRV signal is the lowest.

In an embodiment, there is provided a computer readable recording medium in which a program for implementing the above-described method is recorded.

Advantageous Effects

In accordance with the embodiments of the present disclosure, the system and method for providing VR contents in accordance with an aspect of the present disclosure may measure a change in biological signal of a user in real time, analyze the psychological state of the user according to the biological signal, and provide VR contents to effectively improve the psychological stability of the user based on the analysis result.

Furthermore, the system and method for providing VR contents for relaxation training may acquire a more accurate measurement value for the psychological stability of the user than when only the heart rate or breathing signal of the user is measured.

BRIEF DESCRIPTION OF DRAWINGS

FIGS. 4A and 4B are images showing VR contents which may construct the VR contents for relaxation training in accordance with the embodiment of the present disclosure.

FIG. 5 is a flowchart illustrating a method for providing VR contents for relaxation training in accordance with a first embodiment of the present disclosure.

DETAILED DESCRIPTION OF THE INVENTION

Figure 1:
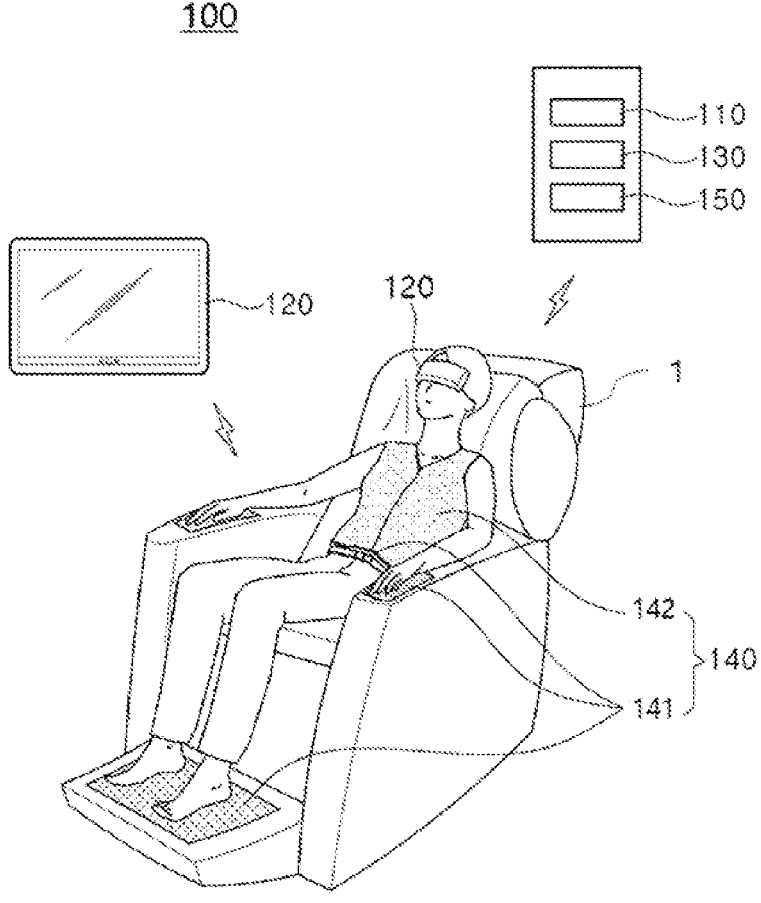
FIG. 1 is a diagram illustrating a system for providing VR contents for relaxation training in accordance with an embodiment of the present disclosure.

The present disclosure relates to a system for providing VR (Virtual Reality) contents for relaxation training to stabilize the psychological state of a user.

In an embodiment, there is provided a system for providing VR (Virtual Reality) contents for relaxation training to stabilize the psychological state of a user. The system may include: a contents providing unit configured to provide VR contents to a user such that the user experiences the VR contents; a VR modeling unit configured to receive information from the user, model the VR contents for stabilizing the psychological state of the user, based on the received user information, and provide the modeled VR contents to the contents providing unit; a biological signal measurement unit configured to measure a biological signal of the user; and a biological signal analysis unit configured to analyze the psychological state of the user according to the experience of the VR contents, based on a change in the measured biological signal of the user. The VR modeling unit may remodel the VR contents according to the psychological state of the user, analyzed by the biological signal analysis unit.

The VR modeling unit may have a plurality of VR contents each composed of a series of images and sounds, extract VR contents suitable for the psychological state of the user, among the plurality of VR contents, based on the user information received from the user, and provide the extracted VR contents to the contents providing unit.

The VR contents may be configured as a video in which an object changes. The VR modeling unit may change the change speed of the object in the video based on the psychological state of the user, analyzed by the biological signal analysis unit, and provide the changed VR contents to the contents providing unit.

The VR modeling unit may analyze the correlation between the VR contents experienced by the user and the psychological stability of the user, analyzed by the biological signal analysis unit, extract the VR contents that have been evaluated to most significantly improve the psychological stability of the user, among the plurality of VR contents, and store the extracted VR contents in a database with the received user information.

Therefore, the system and method for providing VR contents in accordance with an aspect of the present disclosure may measure a change in biological signal of a user in real time, analyze the psychological state of the user according to the biological signal, and provide VR contents to effectively improve the psychological stability of the user based on the analysis result.

The biological signal measurement unit may include: a first sensor module configured to measure a biological signal of the user; and a second sensor module configured to measure an HRV (Heart Rate Variability) signal of the user.

The biological signal analysis unit may determine that the psychological stability of the user is low, when the rate of change in the biological signal of the user, measured by the first sensor module, is 20% higher.

Therefore, the system and method for providing VR contents for relaxation training in accordance with an aspect of the present disclosure may acquire a more accurate measurement value for the psychological stability of the user than when only the heart rate or breathing signal of the user is measured.

In an embodiment, there is provided a method for providing VR contents for relaxation training to a user by using a VR apparatus to stabilize the psychological state of the user. The method may include: providing a plurality of VR contents; an information input step of receiving user information; a first contents providing step of selecting VR contents to stabilize the psychological state of a user according to the received user information, and measuring a biological signal of the user while providing the selected VR contents to the user such that the user experiences the VR contents; an analysis step of calculating a change in the biological signal of the user based on the biological signal of the user, measured in the first contents providing step, and analyzing the psychological state of the user according to the calculated change in the biological signal; and a second contents providing step of changing the VR contents provided in the first contents providing step so as to improve the psychological stability of the user according to the analysis result of the analysis step, and measuring a biological signal of the user.

The method may further include a storage step of analyzing the correlations between the changes in the biological signal of the user, calculated in the first and second VR contents providing steps, and the VR contents provided to the user, extracting the VR contents that have been evaluated to most significantly improve the psychological stability of the user, and storing the extracted VR contents in a database with the received user information.

The analysis step may include determining that the psychological stability of the user is low, when the rate of change in the biological signal of the user is 20% higher, and the VR contents selected in the second contents providing step may be different from the VR contents which are provided in the first contents providing step and in which psychological stability of the user are determined to be low.

The biological signal of the user may include an HRV signal, and the VR contents where the psychological stability of the user may be the highest are VR contents where the LF/HF ratio mean value of the HRV signal is the lowest.

In an embodiment, there is provided a computer readable recording medium in which a program for implementing the above-described method is recorded.

MODE FOR DISCLOSURE

Hereafter, a system and method for providing VR contents for relaxation training in accordance with the present disclosure and components involved in the operation of the system and method for providing VR contents for relaxation training will be described, as concrete contents for carrying out the present disclosure, with reference to the drawings.

Figure 2:
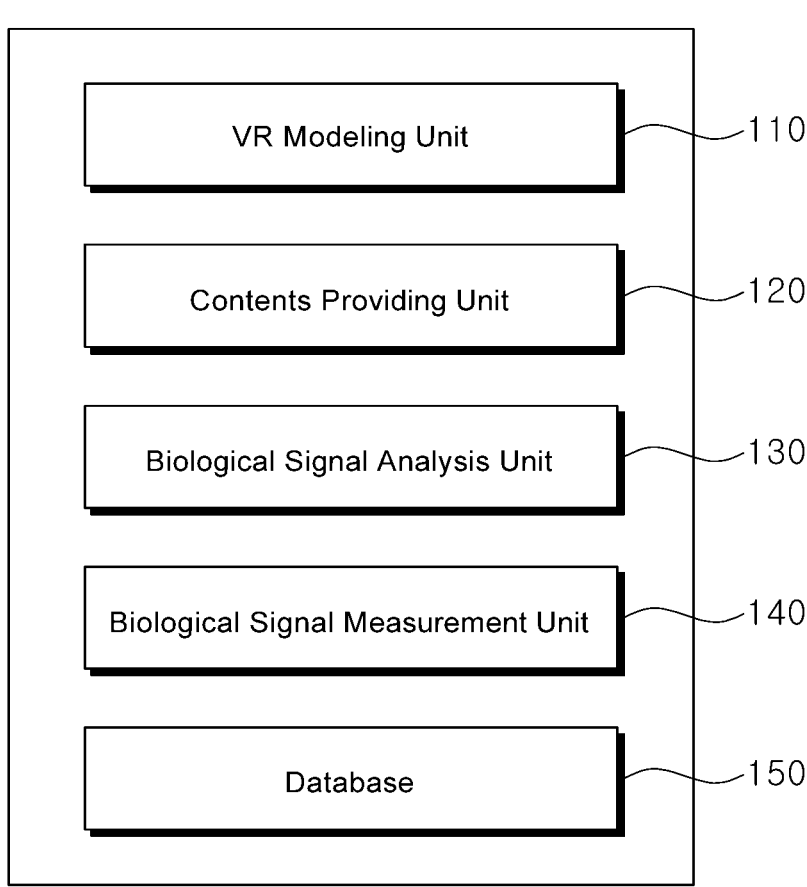
FIG. 2 is a block diagram illustrating the system for providing VR contents for relaxation training in accordance with the embodiment of the present disclosure.

FIG. 1 is a diagram illustrating a system for providing VR contents for relaxation training in accordance with an embodiment of the present disclosure, and FIG. 2 is a block diagram schematically illustrating the configuration of the system for providing VR contents for relaxation training in accordance with the embodiment of the present disclosure. Referring to FIGS. 1 and 2, a system 100 for providing VR contents for relaxation training in accordance with the embodiment of the present disclosure may include a VR modeling unit 110, a contents providing unit 120, a biological signal analysis unit 130 and a biological signal measurement unit 140. The system 100 may further include a database 150.

Referring to FIG. 1, the system for providing VR contents for relaxation training in accordance with the embodiment of the present disclosure may further include a motion chair 1 for further raising the actuality and reality of VR contents provided to a user.

The system for providing VR contents for relaxation training operates as follows. The VR modeling unit 110 analyzes information received from a user through information stored in the database 150, and selectively provides the user with VR contents for relaxation training, suitable for the user, through the contents providing unit 120, while interworking with the contents providing unit 120 and the database 150. The biological signal measurement unit 140 measures a change in biological signal of the user by the VR contents, while interworking with the biological signal analysis unit 130. The biological signal analysis unit 130 analyzes the psychological stability of the user based on the change in biological signal, and transmits the analysis result value to the VR modeling unit 110.

The contents providing unit 120 may be configured to form an image and sound such that the user watches and listens to the image and sound. For example, the contents providing unit 120 is implemented as a device that provides the user with visual data, auditory data, tactile data and the like. In accordance with an embodiment, the contents providing unit 120 may be implemented as a monitor or HMD (Head Mounted Display) which is equipped with a speaker and display and worn by the user. The contents providing unit 120 may be configured to include both of the HMD and the monitor.

Figure 3:
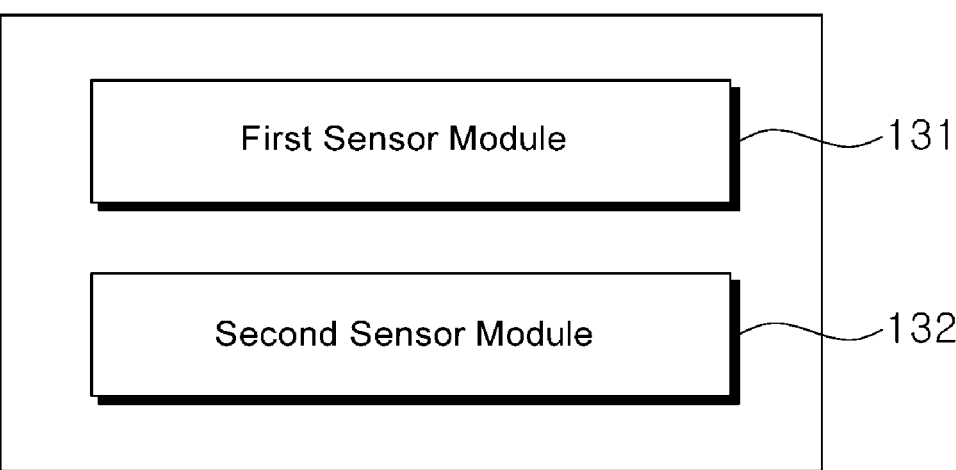
FIG. 3 is a block diagram illustrating a biological signal measurement unit in accordance with the embodiment of the present disclosure.

FIG. 3 is a block diagram illustrating the biological signal measurement unit 140 in accordance with the embodiment of the present disclosure.

Referring to FIG. 3, the biological signal measurement unit 140 in accordance with the embodiment of the present disclosure includes a first sensor module 141 and a second sensor module 142.

In accordance with the embodiment of the present disclosure, the first sensor module 141 includes at least one sensing device configured to measure biological signals such as the electrocardiogram, the breathing capacity and the breathing frequency of the user, and the second sensor module 142 includes at least measurement device configured to measure an HRV (Heart Rate Variability) of the user. The first sensor module 141 and the second sensor module 142 are disposed at the positions where the modules can measure biological signals of the user. For example, the first sensor module 141 may be disposed in a belt of the motion chair 1 or a portion of the motion chair 1, which is touched by the user's arm or leg, and the second sensor module 142 may be disposed in a vest installed in the motion chair 1. However, the positions where the first and second sensor modules are disposed are not limited to the above-described examples, but may be disposed anywhere as long as the first and second sensor modules can measure biological signals of the user.

FIGS. 4A and 4B are images showing VR contents for relaxation training in accordance with the embodiment of the present disclosure.

The relaxation training provided by the present disclosure refers to a training process of training a patient to master a method of relaxing muscles, such that the patient can recover psychological stability by relaxing muscles when facing a psychological problem situation. That is, the contents for relaxation training include contents that guide the user to learn a method of relaxing muscles by repeating a motion of intentionally and gradually contracting the muscles of main body parts and then gradually relieving the muscles.

Furthermore, the VR contents provided by the system in accordance with the embodiment of the present disclosure may include an image that makes the user feel like moving in a specific direction, as an image which is mainly constructed by blue and green backgrounds that are helpful in stabilizing the psychological state of the user. The VR contents may include a visual effect in which the user seems to walk or the body of the user seems to rise by itself. In this case, the VR contents may be formed to show a change to new place or scene with the movement. The image of the VR contents may be changed so that the view of the user is moved forward or vertically, while a change in movement of the image in a side-to-side direction is minimized.

Referring to FIGS. 4A and 4B, the VR contents for relaxation training in accordance with the embodiment of the present disclosure are composed of Stages 1 to 4.

In Stage 1, an image of FIG. 4A, in which a doctor describes a relaxation method, is provided to the contents providing unit 120, with a guide voice to guide a subject to perform the relaxation method.

In Stage 2, images of FIG. 4B, which make the subject feel like slowly flying over tall trees and grass, a road with the sky, a beach with waves, a valley or waterfall at a proper height, are outputted with the visual effect in which the body of the user seems to rise. Then, the user's biological signal is measured.

In Stage 3, the speed at which the subject flies in the sky is reduced, the speed at which the grass trembles is reduced, or the height of the waves is lowered according to the analysis result on the biological signal of the user, measured in Stage 2. Furthermore, the time during which each of the images is provided may be adjusted.

In Stage 4, the correlations between the contents and the user's psychological state are stored in the database 150, while the visual effect in which the user seems to slowly land on the ground is provided.

In Stages 1 to 4, the sounds of nature may also be provided as low sounds suitable for the respective images. Whenever each of the images is changed, a bell sound may come out.

FIG. 5 is a flowchart illustrating a method for providing VR contents for relaxation training in accordance with a first embodiment of the present disclosure.

Referring to FIG. 5, the method for providing VR contents in accordance with the first embodiment includes a first step S100 in which the database 150 stores a plurality of VR contents for relaxation training and receives user information; a second step S200 in which the VR modeling unit 110 selects VR contents for relaxation training, which are configured to stabilize a user's psychological state, according to the user information received by the database 150, combines the selected VR contents and provides the combined VR contents to the user such that the user experiences the VR contents, and the biological signal measurement unit 140 measures a biological signal of the user; a third step S300 in which the biological signal analysis unit 130 calculates a change in biological signal of the user based on the biological signal of the user, measured in the second step, and analyzes the psychological state of the user according to the calculated change in biological signal; and a fourth step S400 in which the VR modeling unit 110 changes the VR contents provided to the user in the second step, in order to improve the psychological stability of the user according to the psychological state of the user, analyzed in the third step, and the biological signal measurement unit 140 measures a biological signal of the user.

The plurality of VR contents provided in the first step include the plurality of VR contents for relaxation training, which are described with reference to FIGS. 4A and 4B. Furthermore, the user information inputted to the database 150 may include the age of the user, the degree of a mental disease, the degree of dizziness and the like. Depending on a situation, the user information may be a medical interview result with a doctor.

In the second step, the plurality of VR contents combined by the VR modeling unit 110 may be composed of different images or formed as consecutive images. The VR modeling unit 110 combines the plurality of visual and auditory data based on the received user information, and outputs the combined data through the contents providing unit 120. For example, when the medical interview result data with the doctor says that the psychological anxiety of the user appears due to specific visual information and auditory information, the VR modeling unit 110 may remove the visual information and the auditory information, or exclude the visual information and the auditory information from the VR contents and then output the resultant VR contents. Furthermore, the VR modeling unit 110 changes the VR contents based on an addition or change of the received user information. For example, when information indicating that the dizziness has been relieved is inputted, the VR modeling unit 110 may change the type, output effect and output time of the VR contents, and then output the changed VR contents.

Furthermore, the VR contents selected by the VR modeling unit include more green or blue backgrounds or have low output speed, as the age of the user is higher, the degree of the depression is higher, and the degree of the dizziness is higher. This is based on a search result saying that an image including more green or blue backgrounds can further stabilize the psychological state of a user, and an image whose output speed is low can further relieve the tension of the user who has relatively severe depression, easily feels dizziness, compared to a strong stimulus such as exposure training.

Furthermore, in the second step, the biological signal measurement unit 140 measures a biological signal of the user according to the VR contents provided to the user through the contents providing unit 120, and transmits the measured data to the biological signal analysis unit 130.

In the third stage, the change in the biological signal may be configured as a breathing period, breathing capacity or heart rate. When the rate of change in the breathing period, the breathing capacity or the heart rate is 20% higher, the VR modeling unit 110 determines that the psychological stability of the user has been lowered.

When the analysis result of the third step indicates that the psychological stability of the user has been lowered, the VR modeling unit 110 changes the VR contents provided in the second step in order to improve the psychological stability of the user, in the fourth step.

For example, the VR modeling unit 110 may change the image of the VR contents to an image including more blue and green backgrounds, or change the chroma and illuminance of the VR contents. Alternatively, the VR modeling unit 110 may repeatedly output the VR contents, which have been evaluated to most significantly improve the stability of the user based on the data stored in the database 150, by a predetermined number of times, or change the current VR contents to the VR contents which have been evaluated to most significantly improve the stability of the user based on the data stored in the database 150, when the psychological stability of the user is not changed or improved while the current VR contents are outputted.

Furthermore, the VR modeling unit 110 may lower the output speed of the provided VR contents, or reduce the change rate of an object included in the VR contents. For example, the VR modeling unit 110 may lower the falling speed of water in an image showing a waterfall, or lower the height of waves in an image of a beach, in order to reduce the change rate of an object in the VR contents.

Figure 6:
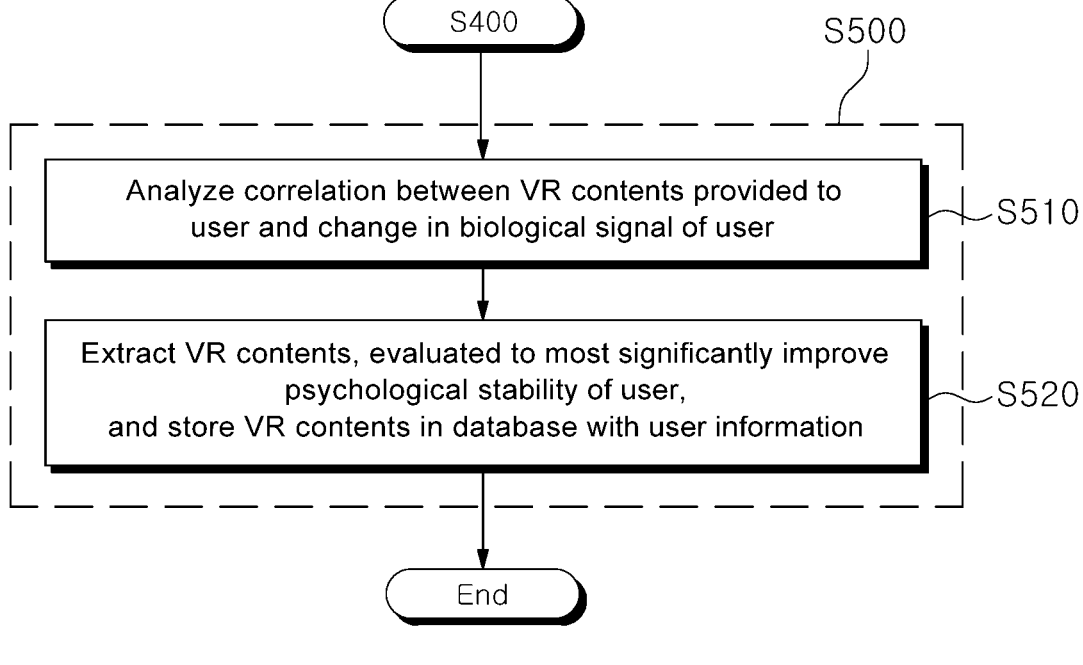
FIG. 6 is a flowchart illustrating a method for providing VR contents for relaxation training in accordance with a second embodiment of the present disclosure.

FIG. 6 is a flowchart illustrating a method for providing VR contents in accordance with a second embodiment of the present disclosure.

Referring to FIG. 6, the method for providing VR contents in accordance with the second embodiment further includes a fifth step S500 of analyzing the correlation between the change in biological signal of the user, calculated in the fourth step S400, and the VR contents provided to the user in the first step S100, extracting VR contents which have been evaluated to most significantly improve the psychological stability of the user, and storing the extracted VR contents and the received user information in the database, in addition to the steps of the first embodiment.

In the fifth step, the extracting of the VR contents that have been evaluated to most significantly improve the psychological stability of the user includes extracting VR contents in which the LF/HF ratio mean value of the HRV signal of the user, measured in the first and fourth steps, is the lowest.

In the fifth step, the information on the VR contents stored in the database with the user information is reused as data for providing VR contents suitable for the user, when the VR contents are provided to the same user again.

So far, the embodiments of the present disclosure have been described. However, the present disclosure is not limited to the configurations of the system for providing VR contents in accordance with the embodiments, but may be variously modified and changed without departing from the scope described in claims.

While various embodiments have been described above, it will be understood to those skilled in the art that the embodiments described are by way of example only. Accordingly, the disclosure described herein should not be limited based on the described embodiments.

The invention claimed is:

1. A non-transitory computer readable recording medium comprising a computer program configured for implementing a method for providing VR (Virtual Reality) contents for relaxation training to a user by using a VR apparatus to stabilize a psychological state of the user, the method comprising:

providing a plurality of the VR contents to the user via a contents providing unit including a speaker and a display, wherein each of the VR contents is configured as a series of images and corresponding sounds;

an information input step of receiving user information;

a first contents providing step of selecting VR contents to stabilize the psychological state of the user according to the information received from the user, and measuring a first biological signal of the user via a first sensor module and a second biological signal of the user via a second sensor module while providing the selected VR contents to the user such that the user experiences the VR contents, the first biological signal being an electrocardiogram, a breathing capacity, or a breathing frequency of the user, and the second biological signal being an HRV (Heart Rate Variability) signal of the user;

an analysis step of calculating in real time a change in at least one of the first or second biological signals of the user, measured in the first contents providing step, and analyzing the psychological state of the user according to the calculated change in at least one of the first or second biological signals of the user, wherein the analysis step comprises determining that the psychological stability of the user is low when a rate of change in the first biological signal of the user, measured by the first sensor module, is at least 20% and determines that the psychological stability of the user is high when an LF/HF (low frequency/high frequency) ratio mean value of the HRV signal, measured by the second sensor module, is low; and a second contents providing step of remodeling the VR contents provided in the first contents providing step so as to improve a psychological stability of the user according to an analysis result of the analysis step, and measuring the biological signal of the user, wherein the sounds comprise a bell sound generated whenever each of the images is changed, wherein the VR contents are configured as a video in which an object changes, wherein the remodeling of the VR contents includes changing a change speed and a dimension of the object in the video based on the psychological state of the user, analyzed in the analysis step, and providing changed VR contents to the contents providing unit.

2. The non-transitory computer readable recording medium of claim 1, the method further comprising a storage step of analyzing correlations between the change in the biological signal of the user, calculated in the first and second VR contents providing steps, extracting the VR contents experienced by the user when the LF/HF ratio mean value of the HRV signal is lowest, and storing the extracted VR contents in a database with the information received from the user.

3. The non-transitory computer readable recording medium of claim 1, wherein the VR contents remodeled in the second contents providing step are different from the VR contents which are provided in the first contents providing step when the psychological stability of the user are determined to be low.

\* \* \* \* \*